United States Patent

Rosowsky et al.

Patent Number: 5,132,414
Date of Patent: Jul. 21, 1992

[54] DIDEOXYNUCLEOSIDE-5'-PHOSPHONO-FORMIC ACID COMPOUNDS

[75] Inventors: Andre Rosowsky, Needham; Ruth M. Ruprecht, Boston, both of Mass.

[73] Assignee: Dana-Farber Cancer Institute, Inc., Boston, Mass.

[21] Appl. No.: 521,748

[22] Filed: May 10, 1990

[51] Int. Cl.$^5$ .............................................. C07H 19/00
[52] U.S. Cl. ........................................ 536/27; 536/28; 536/29
[58] Field of Search .................... 536/27, 28, 29, 23; 514/45, 120

[56] References Cited

U.S. PATENT DOCUMENTS 3,817,982  6/1974  Verheyden et al. ............... 536/23
4,386,081  5/1983  Helgstrand et al. ............... 514/120

FOREIGN PATENT DOCUMENTS 0354246  12/1988  European Pat. Off. .
0355031   8/1989  European Pat. Off. .

OTHER PUBLICATIONS

Rosowsky et al., Biochemical and Biophysical Research Communications 172:288-294, 1990.
European Search Report issued in application No. EP 91 30 4118.2 (1991).
J. Med. Chem., vol. 29, pp. 1389-1393, 1986.
J. Med Chem., vol. 30, pp. 2131-2137, 1987.
CA: vol. 105, No. 11, 97864g, Vaghefi et al., Sep. 15, 1986.
CA: vol. 110, No. 7, 57994w, Lambert et al., Feb. 13, 1989.
New England Journal of Medicine, v 316, pp. 1-8 (by examiner) in Journal, pp. 557-564, Feb. 26, 1987.
Mitsuya et al., Proc. Natl. Acad. Sci. USA vol. 82, 7096-7100 (1985).
Sarin et al., Biochem. Pharmacol. vol. 34, 4075-4079 (1985).
Sandstrom et al., Lancet, vol. 1, 1480-1482 (1985).
Eriksson et al., Antimicrob, Agents Chemother, vol. 33, 663-669 (1989).
Koshida et al., Antimicrob. Agents Chemother., vol. 33, 778-780 (1989).
Vaghefi et al. J. Med. Chem., vol. 29, 1389-1393 (1986).
Griengl et al., J. Med. Chem., vol. 31, 1831-1839 (1988).
Lambert et al., J. Med. Chem., vol. 32, 367-374 (1989).

Primary Examiner—Johnnie R. Brown
Assistant Examiner—James O. Wilson
Attorney, Agent, or Firm—Fish & Richardson

[57] ABSTRACT

Compounds having the structure

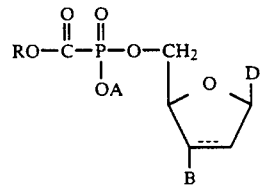

in which R is alkyl, aryl, or aralkyl, A is hydrogen or a water-soluble cation, B is hydrogen, fluorine, or azido, the bond --- is saturated when B is fluorine or azido and is saturated or unsaturated when B is hydrogen, and D is a purine or pyrimidine base are effective inhibitors of retrovirus replication.

6 Claims, 5 Drawing Sheets

DIDEOXYNUCLEOSIDE-5'-PHOSPHONOFORMIC ACID COMPOUNDS

This invention was made with government support and the Federal government has certain rights in the invention.

BACKGROUND OF THE INVENTION

This invention relates to compounds having the structure

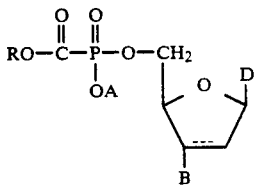

in which R is alkyl, aryl, or aralkyl, A is hydrogen, methyl ethyl or a water-soluble cation such as sodium, ammonium, or quaternary ammonium, or amine, B is hydrogen, fluorine, or azido, the bond --- is saturated when B is fluorine or azido, and is saturated or unsaturated when B is hydrogen, and D is a purine or pyrimidine base. The compounds thus can be considered to be comprised of a 2',3'-dideoxynucleoside molecule covalently bonded to a molecule of phosphonoformic acid partial ester.

Among the most effective drugs available against human immunodeficiency virus (HIV) are those directed against reverse transcriptase, particularly the 2',3'-dideoxynucleosides such as 3'-azidothymidine (AZT) as described by Mitsuya et al., Proc. Natl. Acad. Sci. USA Vol. 82, 7096-7100 (1985). Other agents effective at relatively high concentrations against HIV are salts of phosphonoformic acid (PFA) such as the sodium salt, as described in Sarin et al., Biochem. Pharmacol. Vol 34, 4075-4079 (1985) and by Sandstrom et al., Lancet, Vol. 1, 1480-1482 (1985).

It has also been proposed to employ mixtures of AZT with a very large molar excess of PFA to inhibit replication of HIV or of cytomegalovirus, as described by Eriksson et al., Antimicrob. Agents Chemother. Vol. 33, 633-669 (1989) and by Koshida et al., Antimicrob. Agents Chemother., Vol. 33, 778-780 (1989). Prodrugs of PFA linked to the 5'-hydroxyl of various deoxynucleosides have also been proposed. See Vaghefi, et al. J. Med. Chem., Vol. 29, 1389-1393 (1986); Griengl et al., J. Med. Chem., Vol. 31, 1831-1839 (1988) and Lambert et al., J. Med. Chem., Vol. 32, 367-374 (1989). However, there has been no indication that these prodrugs might have therapeutic activity in cells infected with retroviruses.

It has now been found that a compound having the structure I set forth above and consisting essentially of a phosphonoformic acid partial ester covalently bonded to a 2',3'-dideoxynucleoside in equimolar proportions is more effective than either component alone as an inhibitor of replication of retroviruses, while at the same time exhibiting low toxicity to the host cells.

IN THE DRAWINGS

Figure 1:
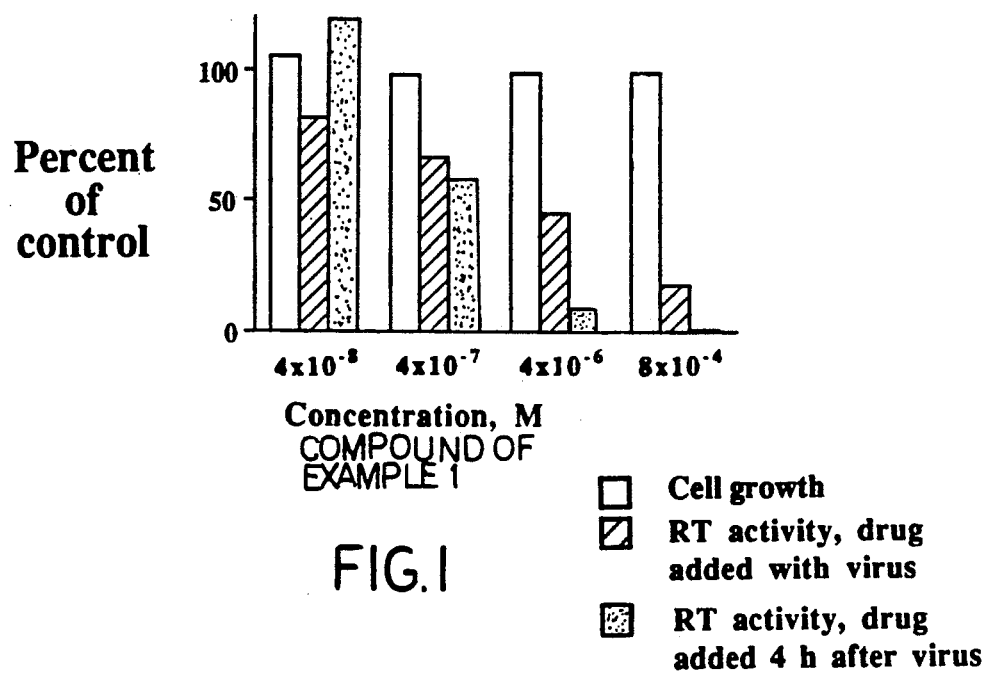
FIG. 1 is a graph showing percent inhibition of HIV-1 replication in Jurkat cells by various concentrations of one embodiment of the invention.

A variety of antiretroviral 2',3'-dideoxynucleosides can form a part of the complex compound of the present invention, among which are those containing a purine or a pyrimidine base such as adenine, guanine, 6-methyladenine, 2-methylguanine, uracil, 5-ethyluracil, thymine, cytosine, and the like; particularly preferred are those containing fluorine or azido in the 3' position.

The phosphonoformic acid partial ester portion of the compound of the present invention contains as the carboxyl ester group R an alkyl group having from one to five carbon atoms, preferably one to three carbon atoms. In addition, the phosphinic acid portion designated A in formula I above may be in the form of the free acid or in the form of a salt of a monovalent cation such as sodium, ammonium or quaternary ammonium, or amine.

The compounds of the present invention may be dissolved or dispersed in any nontoxic pharmacologically acceptable vehicle or carrier, e.g., normal saline, to provide a composition for administration to mammals including humans suffering from infection by immunodeficiency virus or other retroviruses. The relative proportions of the compound and of the vehicle may vary over a wide range and are not critical. The size and rate of dosage may readily be determined by routine tests. Administration may be oral or parenteral.

The compounds of the present invention can be prepared by the general procedure of reacting a trialkyl phosphonoformate with phosphorous pentachloride at room temperature or higher temperatures up to about 100° C., followed by the addition to the reaction mixture, at a low temperature (below 0° C.), of the selected 2',3'-dideoxynucleoside to form a triester having the structure shown in formula I above except that both R and A are alkyl. The triester is then selectively deesterified by reaction with sodium iodide at room temperature or higher in a suitable aprotic solvent, resulting in the desired compound in the form of the sodium salt.

The sodium salt can readily be converted to other desired salts or to the free acid by conventional ion exchange procedures.

The following specific examples are intended to illustrate more fully the nature of the invention without acting as a limitation upon its scope.

EXAMPLE 1

3'-Azido-3'-deoxy-5'-[P-(ethoxycarbonyl)-P-Hydroxyphosphinyl]thymidine, Free Acid (Formula I, R ethyl, A hydrogen, B azide, D thymine). (Ethoxycarbonyl)-phosphonic dichloride (42 mg, 0.22 mmol) was added to a stirred solution of AZT (35 mg, 0.13 mmol) in trimethyl phosphate (0.5 mL) at 0° C. under a nitrogen atmosphere. After 4 h, the reaction mixture was concentrated to dryness with the aid of a vacuum pump. The residue was washed three times with $Et_2O$, dried, and taken up in 80% formic acid (2 mL). The solution was stirred at room temperature for 3 h, then heated to 70° C., and finally allowed to cool slowly to room temperature. The formic acid was removed by vacuum distillation, $H_2O$ (10 mL) was added, and distillation was repeated. Purification of the dried residue, once by flash chromatography on silica gel with 9:1 $CH_2Cl_2$-MeOH as the eluent, and a second time by chromatography on a silica gel minicolumn with 4:1 $CH_2Cl_2$-MeOH, afforded the product as a gum (8 mg, 15% yield). A larger run starting from 228 mg (0.85 mmol) of AZT gave a similar yield.

EXAMPLE 2

3'-Azido-3'-deoxy-5'-[P-methoxy-P-(methoxycarbonyl) phospinyl]thymidine. [Formula I, R and A both methyl, B azido, D thymine.] Phosphorous pentachloride (1.2 g, 5.5 mmol) was added to a solution of trimethyl phosphonoformate (1 g, 6 mmol) in carbon tetrachloride (50 mL), and the suspension was warmed to 50° C. and stirred for 1.5 h. The reaction mixture was evaporated to dryness under reduced pressure, the residue was cooled to −50° C., and a solution of AZT (0.45 g, 1.7 mmol) in dry DMF (10 mL), also pre-cooled to −50° C., was added. After 1 h of stirring at −50° C., the mixture was allowed to come to room temperature and concentrated to dryness under reduced pressure. Flash chromatography of the residue on silica gel (98:2 $CHCl_3$-MeOH) gave a colorless gum (241 mg, 35%); TLC: $R_f$ 0.42 (silica gel, 95:5 $CH_2Cl_2$—MeOH); $^1$H NMR (CDCl$_3$, 60 MHz)δ1.9 (s, 3H, 5—CH$_3$,), 2.4 (m, 2H, C$_2$,—H), 3.8 (s, 3H, C—OCH$_3$), 3.9 (d, J=10 Hz, 3H, P—OCH$_3$), 4.1 (m, 1H, C$_3$,—H), 4.4 (m, 3H, C$_4$,—H, C$_5$,—H), 6.2 (t, 1H, C$_1$,—H), 7.3 (broad s, 1H, C$_6$—H), 9.8 (broad s, 1H, NH). Anal. (C$_{13}$H$_{18}$N$_5$O$_8$P.0.7CH$_2$Cl$_2$.0.5H$_2$O) Calcd: C, 34.86; H, 4.32; N, 14.84; P, 6.57. Found: C, 34.87; H, 3.95; N, 14.90; P, 7.10.

EXAMPLE 3

3'-Azido-3'-deoxy-5'[P-hydroxy-P-(methoxyarbonyl) phosphinyl]thymidine, Ammonium Salt. [Formula I, R methyl, A ammonium, B azido, D thymine.] Sodium iodide (23 mg, 0.15 mmol) was added to a stirred solution of the product of the preceding paragraph (73 mg, 0.17 mmol) in anhydrous tetrahydrofuran (1 mL) and the solution was left to stir under nitrogen at room temperature. After 3 h, the reaction mixture was filtered, and the product in the form of the sodium salt (A=sodium) was washed with anhydrous ether and dried in vacuo; yield 63 mg. Chromatography on a C$_{18}$ silica gel column (10 cm×1 cm) with acetonitrile as the eluent afforded a pale-yellow solid (50 mg) which was taken up in water and applied onto a DEAE-cellulose column (HCO$_3$-form). The product was eluted with 0.05 M ammonium bicarbonate, and TLC-homogeneous fractions were pooled and freeze-dried to the white solid ammonium salt (27 mg, 35%); mp 109°-110° C.; TLC: $R_f$ 0.21 (silica gel, 3:1 CH$_2$Cl$_2$—MeOH); $^1$H NMR (D$_2$O, 300 MHz)δ1.8 (t, 3H, 5—CH$_3$), 2.4 (t, 2H, C$_2$,—H), 3.7 (s, 3H, C—OCH$_3$), 4.1 (m, 3H, C$_3$,—H, C$_5$,—H), 4.4 (m, 1H, C$_4$,—H), 6.2 (t, 1H, C$_1$,—H), 7.6 (s, 1H, C$_6$—H); $^{31}$P NMR (D$_2$O, 121.4 MHz)δ−5.05 (external reference: 1% H$_3$PO$_4$). Anal. (C$_{12}$H$_{16}$N$_5$O$_8$P.NH$_3$.1.25H$_2$O) Calcd: C, 33.60; H, 5.01; N, 19.60; P, 7.23. Found: C, 33.62; H, 4.88; N, 19.77; P, 7.20.

EXAMPLE 4

3'-Azido-3'-deoxy-5'-[P-ethoxy-P-(ethoxycarbonyl) phosphinyl]thymidine. [Formula I, R and A both ethyl, B azido, D thymine.] Triethyl phosphonoformate (0.68 g, 3.2 mmol) was added to a suspension of phosphorous pentachloride (0.65 g, 3.0 mmol) in carbon tetrachloride (20 mL) at 77° C., and the mixture was stirred for 3 h. The reaction mixture was cooled and concentrated to dryness with the aid of a rotary evaporator and vacuum pump. The oily residue was redissolved in DMF (2 mL) cooled to −50° C. in a dry ice-acetone mixture, a precooled (−50° C.) solution of AZT (0.27 g, 1 mmol) in dry DMF (3 mL) was added, and the reaction mixture was allowed to come to room temperature and stirred for 20 h. The resulting solution was concentrated to dryness under reduced pressure, and the residue was purified by flash chromatography on silica gel (98:2 CH$_2$Cl$_2$—MeOH) to obtain the triester as a colorless gum (0.32 g, 75%); TLC: $R_f$ 0.25 (96:4 CH$_2$Cl$_2$—MeOH); $^1$H NMR (CDCl$_3$, 60 MHz)δ1.4 (m, 6H, C—OCH$_2$CH$_3$ and P—OCH$_2$CH$_3$), 1.9 (s, 3H, 5—CH$_3$), 2.2 (m, 2H, C$_2$,—H), 4.3 (m, 8H, C$_3$,—H, C$_4$,—H, C$_5$,—H, C—OCH$_2$CH$_3$, and P—OCH$_2$CH$_3$), 6.2 (t, 1H, C$_1$,—H), 7.4 (s, 1H, 6—H). Anal. (C$_{15}$H$_{22}$N$_5$O$_8$P) Calcd: C, 41.76; H, 5.10; N, 16.24; P, 7.19. Found: C, 41.80; H, 5.31; N, 15.97; P. 7.50.

EXAMPLE 5

3'-Azido-3'-deoxy-5'-[P-(ethoxycarbonyl)-P-hydroxyphosphinyl]thymidine, Ammonium Salt. [Formula I, R is ethyl, A is ammonium, B azido, D thymine.] Sodium iodide (30 mg, 0.24 mmol) was added to a solution of the product of the preceding paragraph (73 mg, 0.17 mmol) in anhydrous tetrahydrofuran (2 mL), and the solution was stirred at room temperature for 20 h. After evaporation of the solvent under reduced pressure, the residue in the form of the sodium salt (A=sodium) was applied onto a DEAE-cellulose column (HCO$_3$-form), and the column was eluted successively with water and 0.05M ammonium bicarbonate. Fractions of the latter eluent containing the product were pooled and freeze-dried to obtain the colorless solid ammonium salt (42 mg, 60% yield); mp 119°-120° C.; TLC: $R_f$ 0.32 (3:1 CH$_2$Cl$_2$—MeOH); HPLC: 11.0 min as compared with 8.0 min for AZT (C$_{18}$ silica gel, 0.01M NH$_4$OAc, pH 6.6, with 5% McCN, 1.0 mL/min); NMR (D$_2$O, 300 MHz)δ1.2 (t, 3H, C—OCH2CH3), 1.8 (s, 3H, 5—CH$_3$), 2.4 (m, 2H, C$_2$,—H), 3.95 (m, 1H, C$_3$,—H), 4.2 (m, 4H, C$_5$,—H, C—OCH2CH$_3$), 4.4 (m, 1H, C$_4$,—H), 6.2 (t, 1H, C$_1$,—H), 7.6 (s, 1H, 6—H). Anal. (C$_{13}$H$_{18}$N$_5$O$_8$P.0.9NH$_3$.1.25H$_2$O) Calcd: C, 35.47; H, 5.09; N, 18.78; P, 7.04. Found: C, 35.47; H, 5.16; N, 18.57; P, 7.25.

The foregoing ammonium salt can readily be converted to the free acid product of Example 1 simply by treatment with an acidic ion-exchange resin.

EXAMPLE 6

2′,3′-Dideoxy-5′-[P-(ethoxycarbonyl)-P-hydroxyphosphinyl]cytidine, Ammonium Salt (Formula I, R ethyl, A ammonium, B hydrogen, ≡≡≡ bond saturated, D cytosin-1-yl). Triethyl phosphonoformate (0.3 g, 1.4 mmol) and phosphorous pentachloride (0.3 g, 1.4 mmol) were heated in carbon tetrachloride (15 mL) at the reflux temperature for 3 h, and the reaction mixture was cooled to room temperature and concentrated to dryness under reduced pressure. The residue was taken up in DMF (3 mL), the solution was cooled to $-50°$ C., and 2′,3′-dideoxycytidine (0.1 g, 0.47 mmol) was added under a dry nitrogen atmosphere. The reaction mixture was allowed to come to room temperature, and after 2 h the solvent was removed in vacuo. The residue was taken up directly in anhydrous tetrahydrofuran (4 mL) containing sodium iodide (65 mg, 0.43 mmol), and the mixture was stirred at room temperature for 20 h. After evaporation of the reaction mixture to dryness, the residue was applied onto a DEAE-cellulose column ($HCO_3$-form), and the column was eluted first with water and then with 0.05M $NH_4HCO_3$. Appropriate fractions were pooled and freeze-dried to obtain a white solid (0.1 g) which was further purified by preparative HPLC on $C_{18}$ silica gel, with 5% MeCN in 0.01M $NH_4OAc$ as the eluent. Freeze-drying of the principal fraction afforded the product as a white solid (50 mg, 29% overall yield based on 2′,3′-dideoxycytidine); mp 148°–150° C. Anal. ($C_{11}H_{18}N_3O_6 \cdot 0.4NH_3 \cdot 1.25H_2O$) Calcd: C, 38.26; H, 5.77; N, 12.65; P 8.23. Found: C, 38.17; H, 5.73; N, 12.66; P. 8.03.

For biological testing, a stock solution of the free acid of Example 1 was made up in DMSO and dispensed into RPMI 1640 cell growth medium to give the desired range of concentrations. The final DMSO concentration in the medium was <0.1%. These solutions in cell growth medium were used in all of the biological tests described below.

The compound of Example 1 was tested initially for its ability to inhibit HIV-1 replication in Jurkat cells, a CD4+ human T-lymphocyte line commonly used for this purpose. Reverse transcriptase (RT) activity in the supernatant from the infected cells was used as a measure of viral replication, and the compound was added to the cultures at time zero or 4 h post-infection. Parallel cytotoxicity assays were performed in non-infected Jurkat cells to assess therapeutic selectivity. As shown in FIG. 1, cell viability was decreased after 4 days exposure by less than 10% at drug concentrations of up to $10^{-4}M$. In contrast, 50% inhibition of RT activity relative to non-treated HIV-infected cells was observed at a concentration of approximately $5 \times 10^{-7}M$. This showed the compound to be both active and selective, when given to cells at the same time as virus or 4 h later.

Figure 2A:
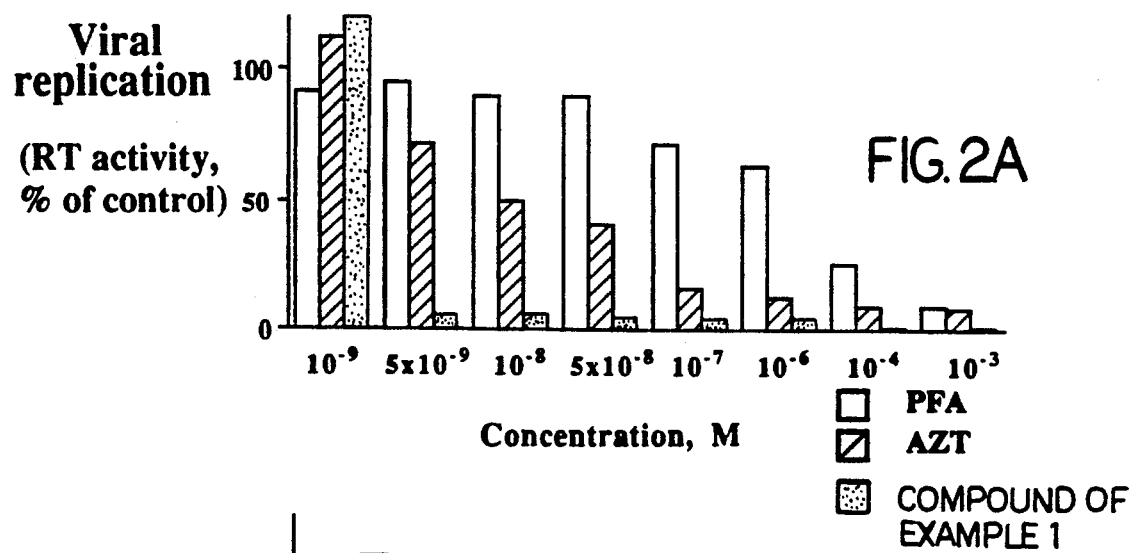
FIG. 2A is a graph showing inhibition of HIV-1 replication in Jurkat cells by PFA, by AZT, and by one embodiment of the invention, each added 4 hours before the HIV-1 and kept present continuously throughout the duration of the experiment.
Figure 2B:
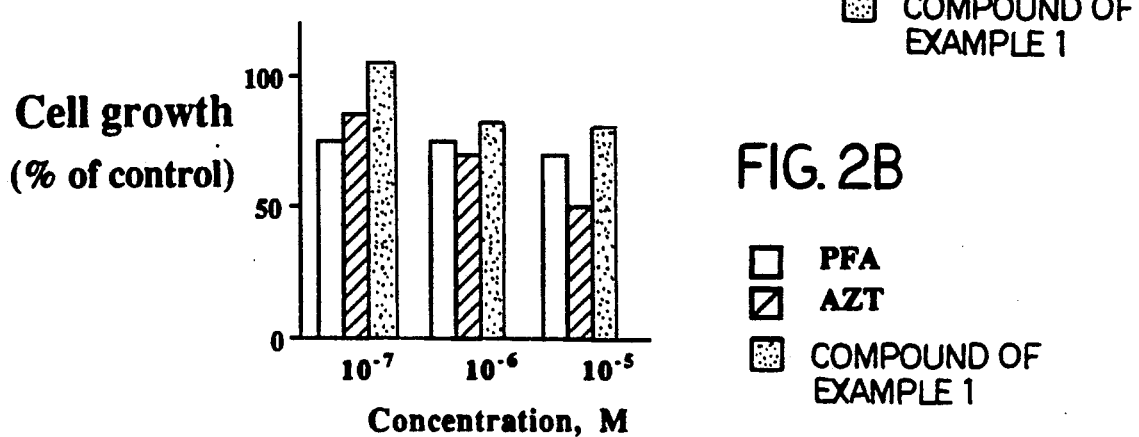
FIG. 2B is a graph showing inhibition of Jurkat cell growth under the same conditions as in FIG. 2A.

In a second evaluation, the compound salt of Example 1, AZT, and PFA were compared as inhibitors of HIV-1 replication in Jurkat cells when added to the cultures 4 h before the virus (i.e., in a prophylaxis model). The drugs were present through the length of the experiment (4 days). As shown in FIG. 2A, RT activity in culture supernatants decreased to 50% of control values at AZT and PFA concentrations of $10^{-8}$ and $10^{-5}M$, respectively. In contrast, the 50% inhibitory concentration ($IC_{50}$) for the compound of Example 1 was estimated to be $2 \times 10^{-9}M$, a roughly fivefold increase in potency relative to AZT, and there was >95% inhibition of RT activity at $5 \times 10^{-9}M$, whereas the concentrations of AZT and PFA needed to achieve the same degree of inhibition were $10^{-4}$ and $10^{-3}M$, respectively. In addition to being more potent than AZT or PFA in its antiviral activity, the compound of Example 1 was relatively non-toxic to host cells, giving only 20% growth inhibition at $10^{-5}M$ as compared with 50–60% inhibition by AZT and 30% inhibition by PFA at the same concentration. Because of its higher antiviral potency and lower cytotoxicity, the compound of Example 1 appeared to have substantially more favorable therapeutic index (TI), defined as the $IC_{50}$(antiviral activity)/$IC_{50}$(cell growth inhibition) ratio. Thus, while there was an approximately four-log TI for AZT in this experiment, the TI for the compound of Example 1 could not actually be estimated because the $IC_{50}$ for cell growth inhibition, extrapolated from the dose-response curve, was $>10^{-3}M$.

Figure 3A:
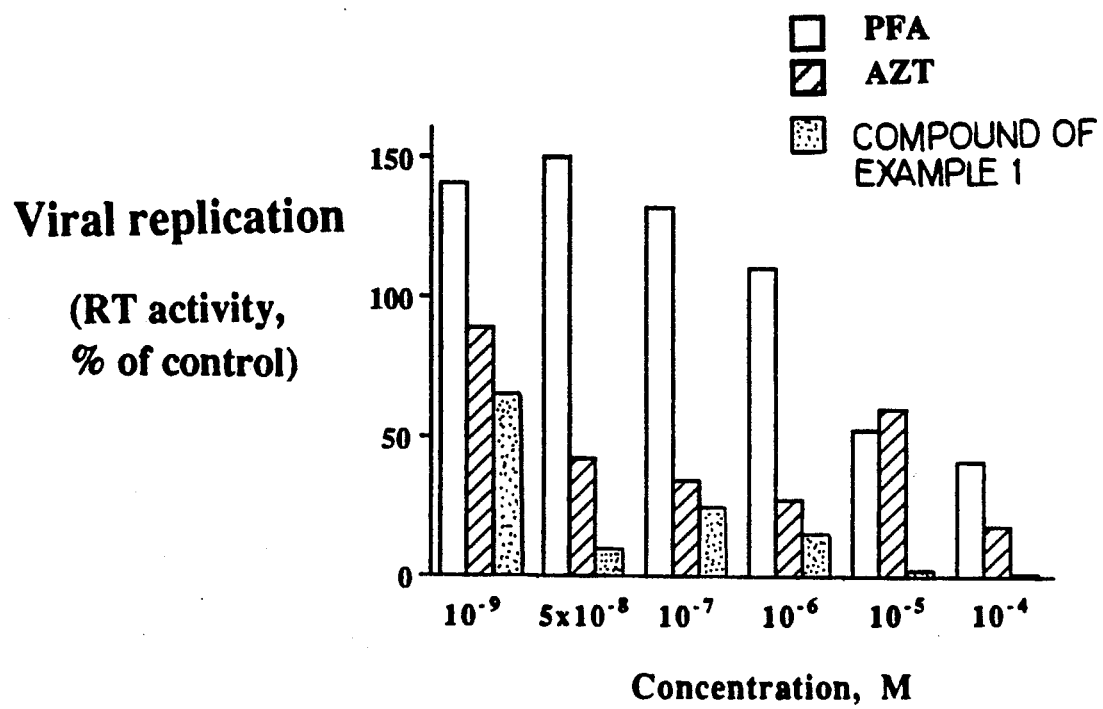
FIG. 3A is a graph showing inhibition of HIV-1 replication in human peripheral blood leukocytes.
Figure 3B:
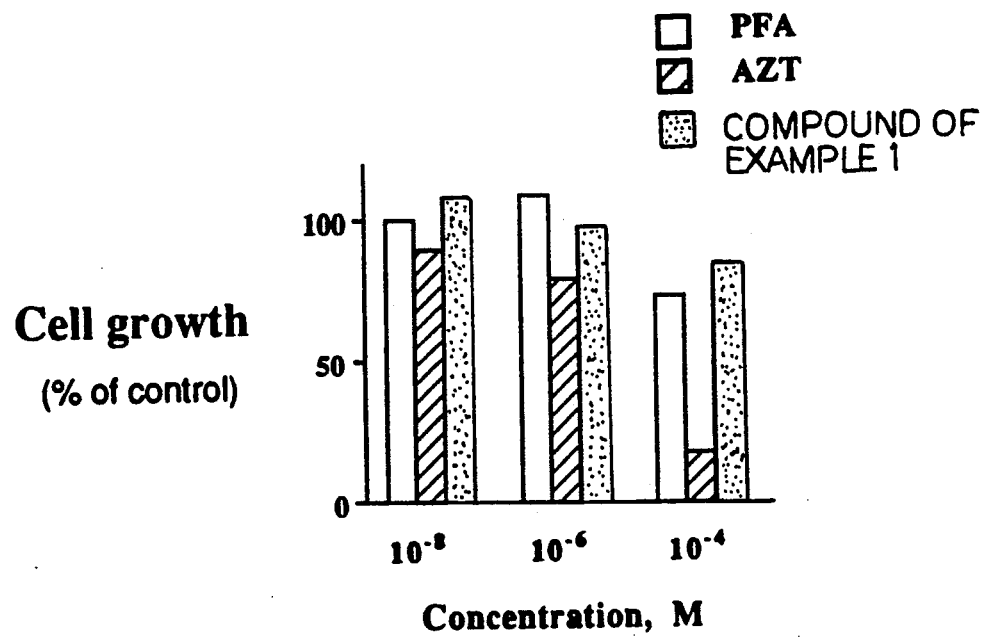
FIG. 3B is a graph showing inhibition of growth of human peripheral blood leukocytes.

The activities of the compound of Example 1, AZT, and PFA were also examined in cultured human peripheral blood leukocytes (H-PBLs) infected with HIV-1. As shown in FIG. 3A, AZT and the compound of Example 1 both inhibited viral replication by about 50% at a concentration of $10^{-8}M$ when added to the cultures 4 hours before the virus and measured at 4 days. However, as shown in FIG. 3B, whereas AZT inhibited PBL growth by 80% at $10^{-4}M$, there was only 20% inhibition by the same concentration of the compound of Example 1. In both PBLs and Jurkat cells, therefore, the antiviral potency of the compound of Example 1 resembled that of AZT, while its low cytotoxicity was more reminiscent of that of PFA.

Figure 4A:
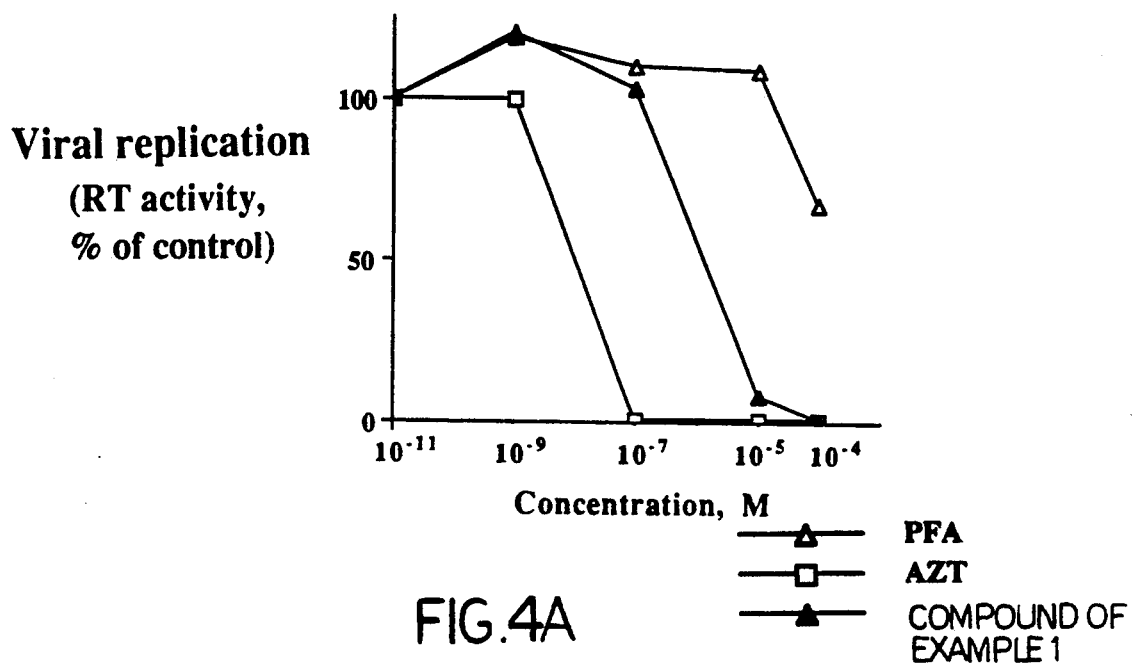
FIG. 4A is a graph showing inhibition of plaque formation by a different retrovirus (a murine leukemia virus) in mouse fibroblast cultures.
Figure 4B:
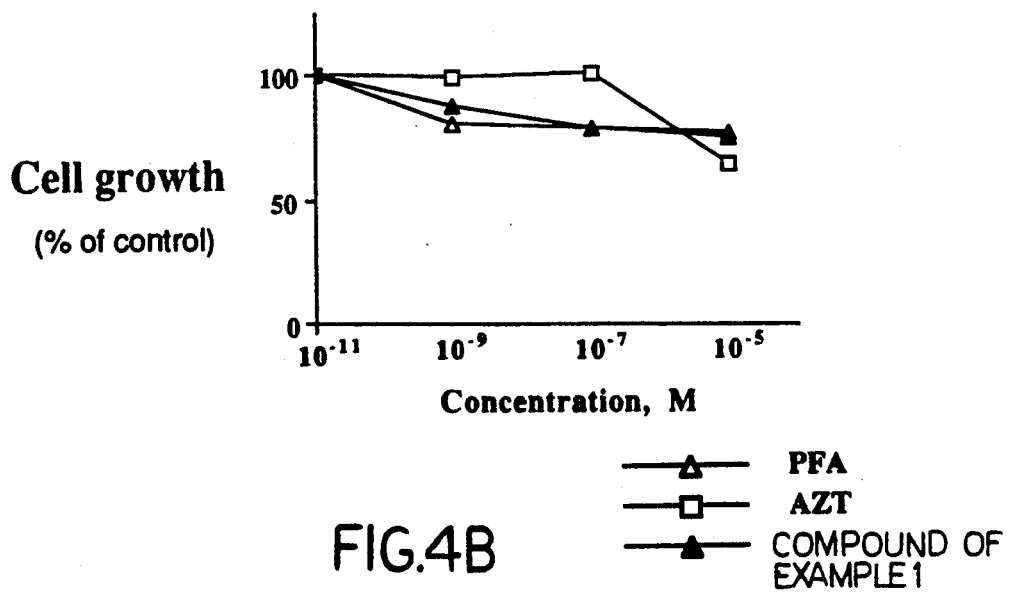
FIG. 4B is a graph showing inhibition of growth in mouse fibroblast cultures under the same conditions as in FIG. 4A.

The compound of Example 1 as well as AZT and PFA were also tested in a plaque assay for the ability to inhibit plaque formation in mouse fibroblast cultures by Rauscher murine leukemia virus (RLV), a type C retrovirus; the results are shown in FIG. 4A. Drugs were added to the cultures 4 hours before the virus, and inhibition was measured at 4 days. The cytotoxicity of all the agents to non-infected fibroblasts was also determined and found to be <50% at concentrations of up to $10^{-5}M$ as shown in FIG. 4B. Complete inhibition of plaque formation was observed with $10^{-7}M$ AZT, but there was no appreciable effect with PFA itself until the concentration reached $10^{-4}M$, as shown in FIG. 4A. When AZT alone was used at a concentration of only $10^{-9}M$ there was no effect, but when AZT and PFA were combined, each at concentrations of $10^{-9}M$, there was almost 50% inhibition of plaque formation even though the PFA was not used in excess. The compound of Example 1 produced almost complete inhibition of plaque formation at $10^{-5}M$, but was inactive at $10^{-7}M$ as shown in FIG. 4A. Thus, in the RLV system, this compound was less effective than AZT or a 1:1 combination of AZT and PFA.

Figure 5A:
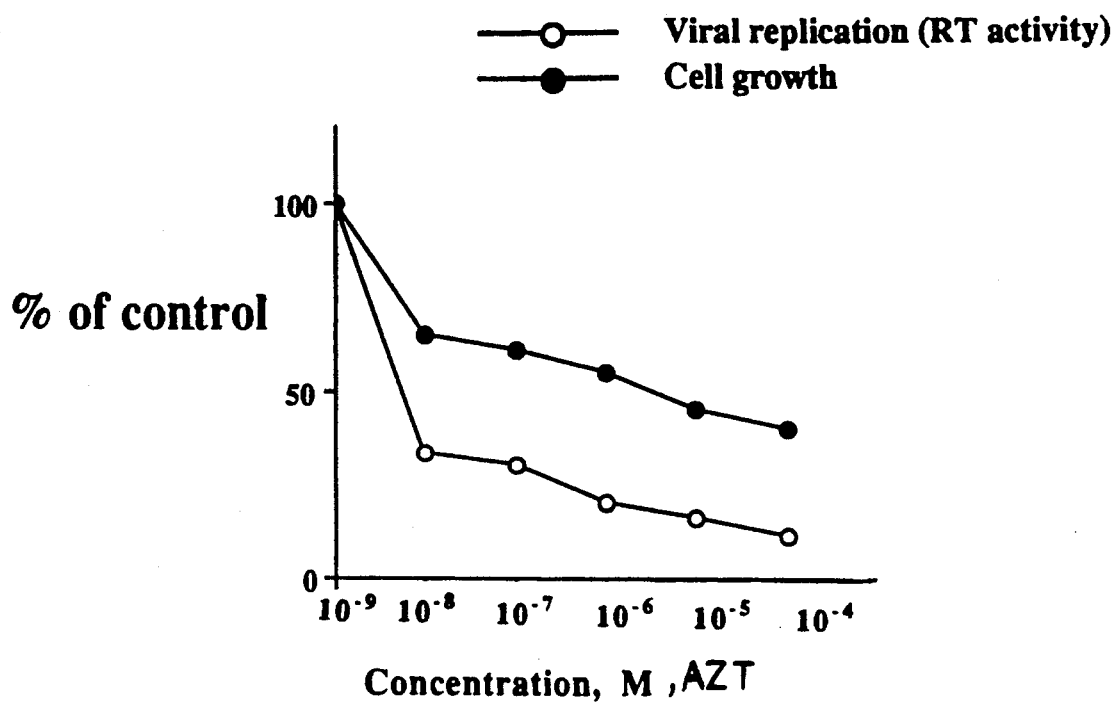
FIG. 5A is a graph showing inhibition by AZT of retroviral propagation and of cell growth in cultured human lymphoblasts infected with simian immuno-deficiency virus.
Figure 5B:
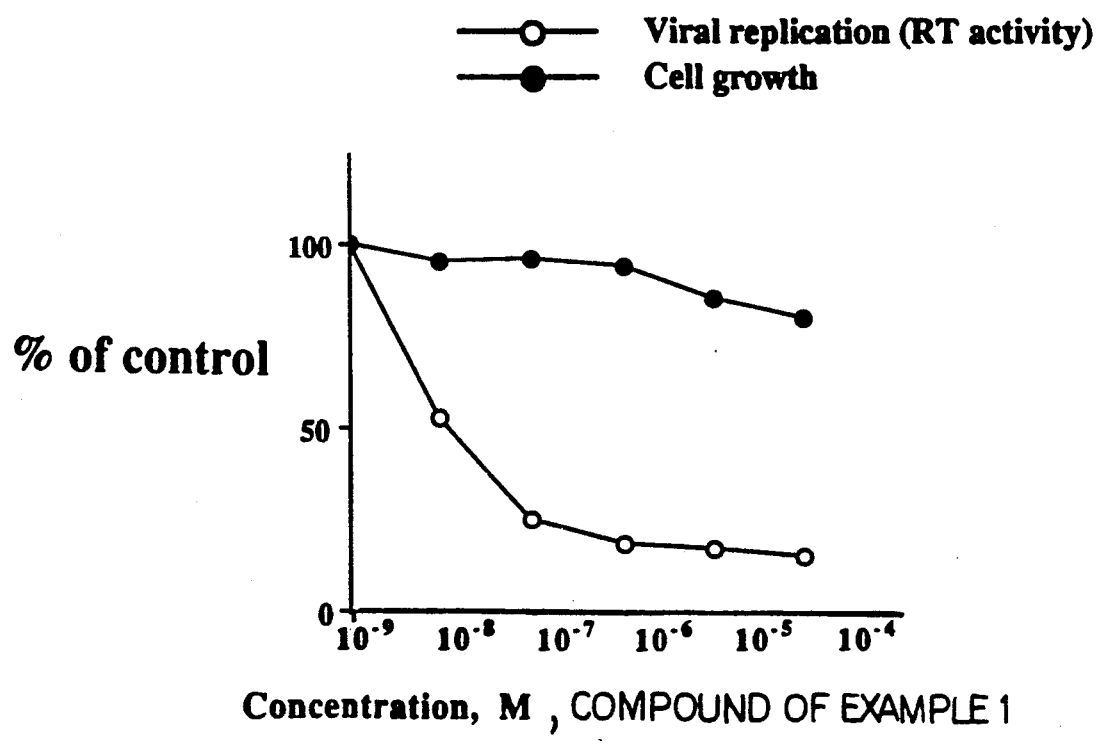
FIG. 5B is a graph showing the results of using one embodiment of the invention in the same test as that of FIG. 5A.

The activities of AZT and of the compound of Example 1 against simian immunodeficiency virus (SIV) in cultured human lymphoblasts (CEM cells) were assayed; the results are shown in FIGS. 5A and 5B, respectively. The drugs were added to the culture 4 hours before the virus and inhibition was measured at 3 days. As shown in FIG. 5A, the approximate $IC_{50}$ values for inhibition of RT activity in cultures of SIV-infected CEM cells and for CEM cell growth by AZT were $5 \times 10^{-9}$ and $2 \times 10^{-6}$M, respectively. The corresponding values for the compound of Example 1 as shown in FIG. 5B were $1 \times 10^{-8}$ and $>10^{-4}$M; thus, both had similar activity as inhibitors of viral replication, but the latter compound was at least 200 times less toxic to the host cells, resulting in a substantially higher TI.

Figure 6A:
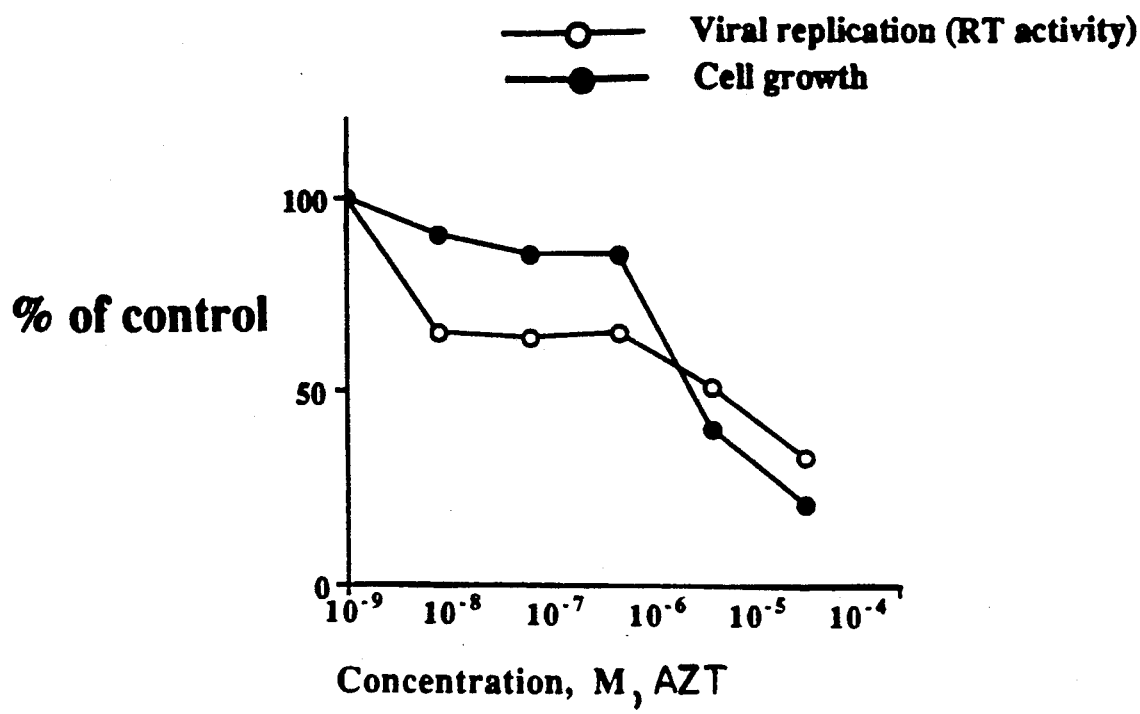
FIG. 6A is a graph showing results of a test similar to that of FIG. 5A except that monkey peripheral blood leukocytes were used.
Figure 6B:
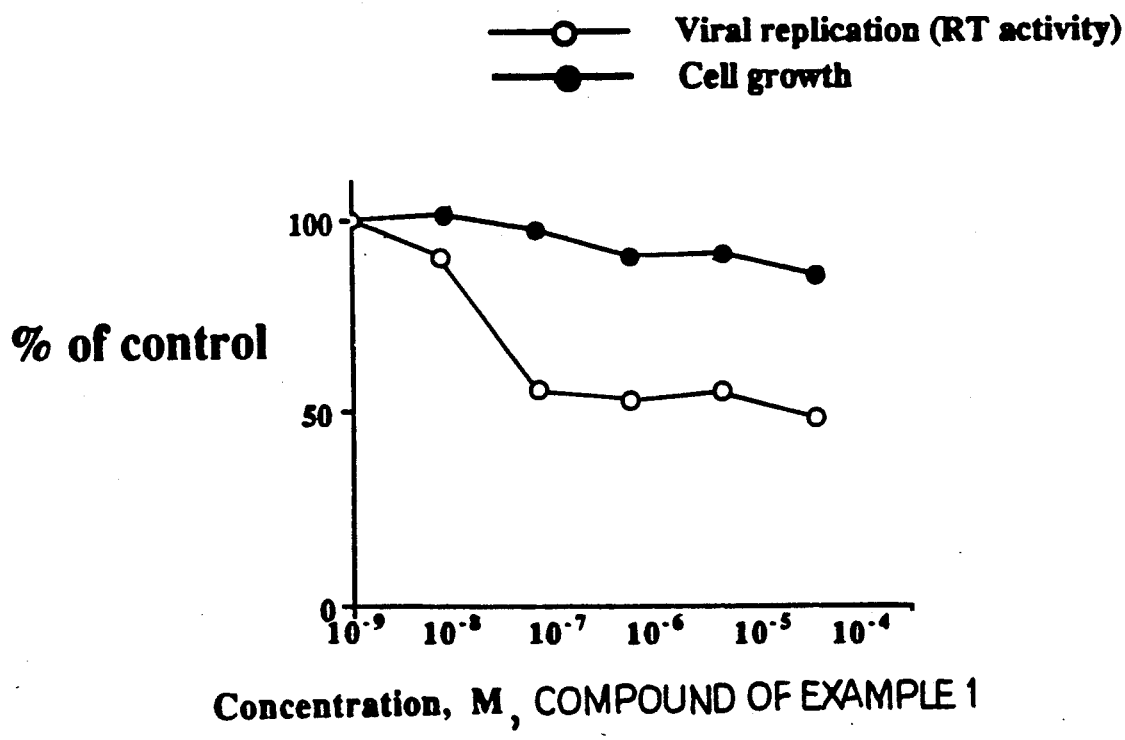
FIG. 6B is a graph showing inhibition by one embodiment of the invention under the same conditions as in FIG. 5B.

Inhibition of SIV replication as well as cell growth required higher AZT concentrations when tested in cultures of monkey peripheral blood leukocytes (M-PBLS) under the same conditions, as shown in FIG. 6A, indicating that bioconversion of AZT to AZT triphosphate (AZTTP) was probably less efficient in these monkey cells than in the human cells. The effect of the compound of Example 1 on SIV replication in M-PBLs as shown in FIG. 6B was somewhat similar to that of AZT, giving 50% inhibition of RT activity at a concentration of $10^{-7}$M. However, it appeared once again in FIG. 6B that toxicity to the host cell was considerably lower than with AZT, resulting in a more favorable TI.

To examine the question whether RT inhibition by the compound of Example 1 could by itself account for the antiretroviral effect in intact cells, the effect of the compound on RT activity was examined in a cell-free assay with purified HIV-1 RT. An IC$_{50}$ value (ca. 50 μM) well in excess of the concentration needed to block viral replication was obtained. Therefore, it appears that metabolism is required in the action of the compound of Example 1 or that the compound has one or more targets other than RT in the cell.

Similar biological activities and properties can be found in the compound of Example 2-6 and other compounds of the present invention.

What is claimed is:

1. A compound having the structure

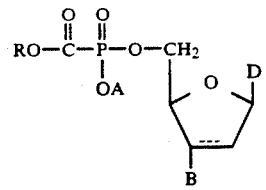

in which R is alkyl having one to five carbon atoms, A is hydrogen, methyl, ethyl, or a water-soluble cation, B is hydrogen, fluorine, or azido, the bond --- is saturated when B is fluorine or azido and is saturated or unsaturated when B is hydrogen, D is a purine or pyrimidine base.

2. A compound as claimed in claim 1 in which R is methyl, A is ammonium, B is azido, and D is thymine.

3. A compound as claimed in claim 1 in which R is ethyl, A is ammonium, B is azido, and D is thymine.

4. A compound as claimed in claim 1 in which R is ethyl, A is ammonium, B is hydrogen, the bond --- is saturated, and D is cytosine.

5. The compound of claim 1 wherein R is methyl.

6. The compound of claim 1 wherein R is ethyl.

* * * * *

UNITED STATES PATENT AND TRADEMARK OFFICE
CERTIFICATE OF CORRECTION

PATENT NO. : 5,132,414

DATED : July 21, 1992

INVENTOR(S) : Andre Rosowsky, Ruth Ruprecht and Jayanta Saha

It is certified that error appears in the above-identified patent and that said Letters Patent are hereby corrected as shown below:

On cover page, please add the following to Section [75] Inventor: --and Jayanta Saha, Cambridge, MA--

Signed and Sealed this

Eighteenth Day of January, 1994

Attest:

BRUCE LEHMAN

*Attesting Officer*   *Commissioner of Patents and Trademarks*